United States Patent [19]

Behrend

[11] Patent Number: 4,739,532

[45] Date of Patent: Apr. 26, 1988

[54] BRISTLE SHAFT BUNDLE AND BRISTLE SHAFT EQUIPMENT FOR THE TOTAL SUBGINGIVAL CLEANSING OF PERIODONTAL POCKETS, PARODONTAL POCKET EDGES AND ALL DENTAL SURFACES

[76] Inventor: Hans Behrend, Schulzendorfer Str. 17, 1 Berlin 65, Fed. Rep. of Germany

[21] Appl. No.: 2,863

[22] Filed: Jan. 13, 1987

[51] Int. Cl.[4] .......................................... A46B 13/02
[52] U.S. Cl. ........................................ 15/28; 15/180; 433/166
[58] Field of Search .................. 15/28, 29, 179, 180, 15/198; 433/166

[56] References Cited

U.S. PATENT DOCUMENTS 3,404,422 10/1968 Warner ................................. 15/180
4,020,522 5/1977 Behrend .............................. 15/28

FOREIGN PATENT DOCUMENTS 6707641 12/1967 Netherlands ........................ 15/28

*Primary Examiner*—Peter Feldman
*Attorney, Agent, or Firm*—Michael J. Striker

[57] ABSTRACT

A bristle shaft device for use in disinfecting subgingival parodontal pockets, parodontal pocket edges and tooth surfaces, the device having a rotationally symmetrical gingival edge cup having an axis and an external periphery and a plurality of coaxial bristle shafts arranged coaxially in a ring and held in position by the cup. The shafts project from the external periphery and are formed as individual radially adjacent layers. One of the layers extend beyond the other layers so as to have an exposed end and can penetrate into a subgingival parodontal pocket up to a ligamentum circulare. Another layer adjacent to the one layer resists a bending of the exposed layer. The remaining layers are formed as multiple stepped layers that drop off in steps from each other in a radially outward direction providing further reinforcement. The one layer is radially innermost of the rest of the layers. Both the one layer and the adjacent another layer project beyond the remaining layers. The exposed end of the one layer is formed with a projection so as to form an individual, coaxial bristle shaft ring.

17 Claims, 1 Drawing Sheet

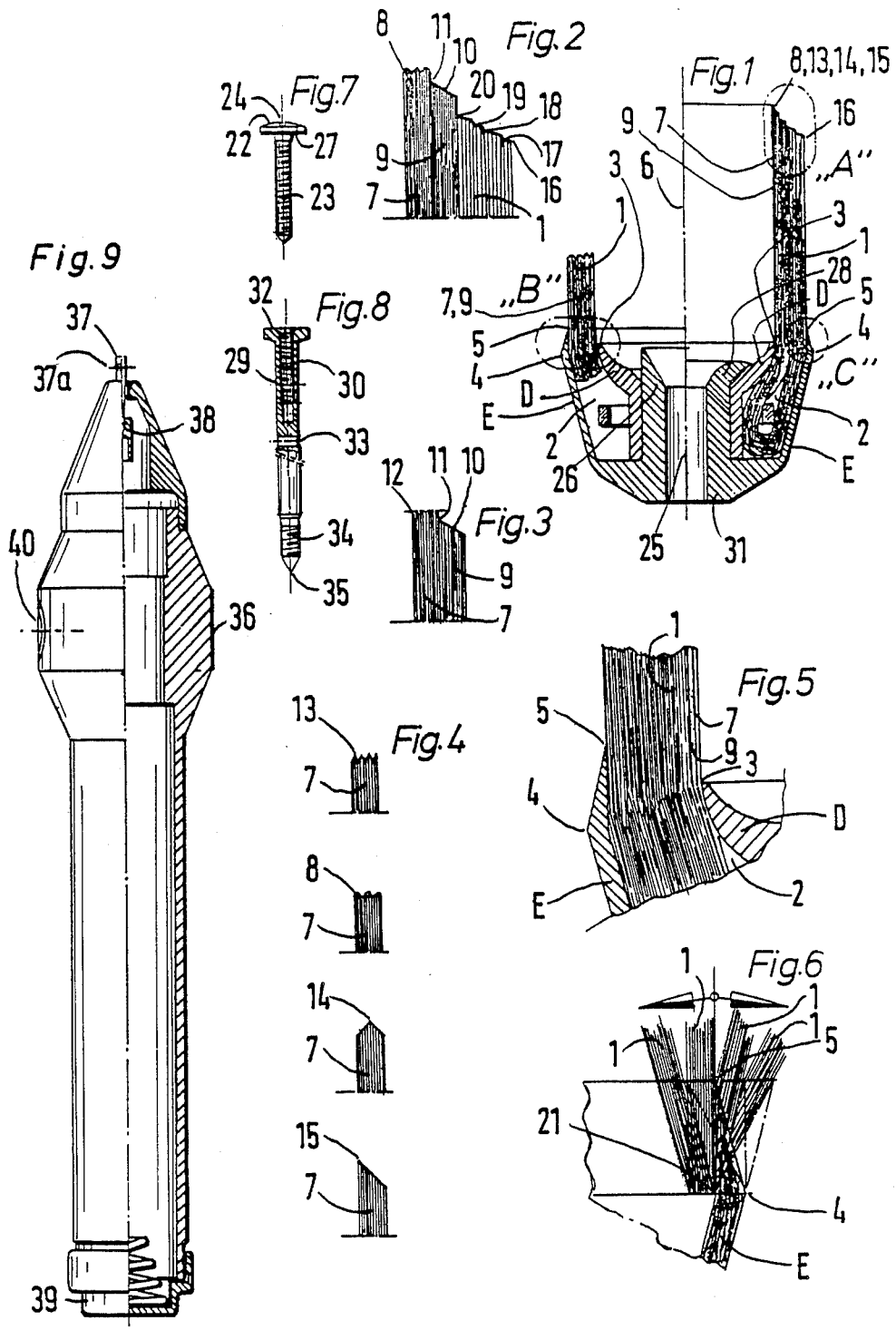

BRISTLE SHAFT BUNDLE AND BRISTLE SHAFT EQUIPMENT FOR THE TOTAL SUBGINGIVAL CLEANSING OF PERIODONTAL POCKETS, PARODONTAL POCKET EDGES AND ALL DENTAL SURFACES

BACKGROUND OF THE INVENTION

The present invention relates to a bristle shaft device for subgingival treatment of parodontal pockets.

The invention is based on a new concept: "Health instruction in the field of periodontal pockets" for permanent teeth in the open space of the human mouth and solves this problem by means of a revolutionary new therapy, the use of which puts a stop to the advance of the bacterial process of destruction on all 32 periodontal pockets which exist around the tooth necks.

To achieve this the latest state of the art has shown that instead of caring for the teeth by cleaning, residual food containing carbohydrates should be removed daily from the subgingival gap of the periodontal pocket between the tooth enamel and the ephithelial tissue, this being carried out from the ligamentum circulare towards the tooth crown surface in order to protect the connective tissue fibre of the dental periosteum, from which emerge numerous Sharpey fibres into the dental root cement, from substances which cause rot and decay.

Teeth require such biological disinfection because the force arising due to the process of chewing presses the masticated food up into the most remote corners to the ligamentum circulare, this process of accumulation and deposit causing fermentation substances and acids to arise which in the long run act on the hard thin substance of the tooth enamel which coats the tooth completely and which is composed of approx. 88% calcium phosphate, 2% organic substances, 1.5% magnesium phosphate, 0.3% calcium fluoride and 0.2% fat.

In addition due to infection they also lead to inflammation of the connective tissue fibres of the dental periosteum and the Sharpey fibre, thus thwarting the purpose of the firm and inherent connection of the two tissues to the root cement and the bone wall of the alveola as well as the alveolar septa in the inter-radicular space.

Cleaning the teeth daily only leads to a lack of mouth secretion and acid on the tooth enamel; the chemical influences and acids between the epithelium and tooth enamel which are not naturally interconnected have thus remained unaffected to the present day.

The techniques employed for tooth care in the USA and the Federal Republic of Germany as well as other countries all over the world using tooth brushes or rotation cups fitted with brush arrangements, published in U.S. Pat. Nos. 3,335,444 and 3,177,510 and DE-PS 24 61 053 C2 are ineffective because by this technique it is only possible to clean the tooth crown surfaces, to disinfect the periodontal pocket rim and to massage the external gums with their mucous membrane.

Daily disinfection of the periodontal pockets represents a contrasting approach which will offer resistance to the universal sickness of bad teeth and which will be of great benefit to humanity.

SUMMARY OF THE INVENTION

It is an object of the present invention to provide a device for daily disinfecting subgingival pockets to combat tooth decay and disease.

This and other objects are attained by a bristle shaft device for use in disinfecting subgingival periodontal pockets, parodontal pocket edges and dental surfaces, the device having a rotationally symmetric gingival edge cup having an axis and an external periphery and a plurality of coaxial bristle shafts arranged coaxially in a ring and held in position by the cup. The shafts project from the external periphery and are formed as individual radially adjacent layers. One of the layers extend beyond the other layers so as to have an exposed end and can penetrate into a subgingival parodontal pocket up to a ligamentum circulare. Another layer adjacent to the one layer resists a bending of the exposed layer. The remaining layers are formed as multiple stepped layers that drop off in steps from each other in a radially outward direction providing further reinforcement. The one layer is radially innermost of the rest of the layers. Both the one layer and the adjacent another layer project beyond the remaining layers. The exposed end of the one layer is formed with a projection so as to form an individual, coaxial bristle shaft ring.

Tooth decay and periodontopathic disorders arise due to unemptied and non-disinfected subgingival periodontal pockets in which accumulations and deposits of masticated food containing carbohydrates on the ligamentum circulare cannot be removed by traditional methods and means of daily tooth care. For the first time the nature of the incidence of tooth decay and periodontopathic disorders and in particular their reason for arisal has thus been proved and explained scientifically.

Due to scientific advances in the application of such a hi-tech products as bristle shaft devices intensive care is provided between the tooth enamel and the epithelial tissue up to the ligamentum circulare because in accordance with the invention the appropriately shaped bristle shaft tips not only remove the mucous secretion but also help to bring about definitive healing of alveolar pyorrhoea without any irritation by additional antiseptics.

For rotating penetration to the ligamentum circulare a natural, individual, reinforced, rotationally circular-bristle shaft is provided which consists of piled-up keratinised cells, a medullary strand, a cortical layer, and an outer skin of average hardness; this is obtained by a specific shaft section and a bristle shaft bundle arranged coaxially into a gingival rim cup.

The procedure of raising accumulated and deposited substance which cause decay from the subgingival periodontal pockets on to the tooth crown surfaces as well as the process of rinsing the tooth surfaces is carried out in one operation by gentle control of the periodontal pocket device by the user himself by applying the bristle shaft device 8 shown in the enlargement FIG. 2 of detail "A" in accordance with FIG. 1 on the periodontal pocket rim (marginal gingiva). As a result of this the tooth surfaces in the conic trapeze space 6 are included and in the course of the two-fold rotation process the following effects are brought about in one smooth operation taking about 40 seconds:
Protection from decalcification of tooth enamel,
Protection from decay incidence
Protection from inflammation of ligamentum circulare, Protection from alveolar phorrhoea (paradontitis, periodontal disorders), Protection from soft tooth plaque deposits and bad breath, Visibility of dentin tooth colour due to transparency of the tooth enamel.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 1 is an enlarged view of two combined axial sections through a conic trapezium-shaped bristle shaft wherein, on the left the shaft is shown in the premounted state and on the right the shaft is in an already flanged-in state;

FIG. 2 is an enlarged view of detail "A" of FIG. 1 showing a bristle shaft arrangement of the innermost bristle shaft corrugated ring layer and the overall bristle shaft bundle steps;

FIG. 3 is an enlarged view of detail "A" of FIG. 1 showing the upper cross-section of the innermost individual rotationally circular reinforced bristle shaft;

FIG. 4 is an enlarged view of detail "A" of FIG. 1 showing four of the wide variety of possible bristle shaft arrangements in the cross-section plane;

FIG. 5 is an enlarged view of detail "A" of FIG. 1 showing the cup ring blade of the inner cup and the cup ring blade of the outer cup;

FIG. 6 is an enlarged view of detail "C" of FIG. 1 wherein four of many possible variations are shown;

FIG. 7 shows a side view of the securing screw of the gingival rim cup in the shaft carrier;

FIG. 8 shows an elevation view, partially in section, of the shaft carrier for transmitting the rotary motion of the motor to the gingival rim cup; and FIG. 9 shows an elevational view, half in section, of the carrier and drive casing.

DETAILED DESCRIPTION OF THE PREFERRED EMBODIMENTS

FIG. 1 shows a conic trapeze shaped, rotationally round, reinforced, individual, innermost bristle shaft with corrugated or zig-zag, roof-shaped and pointed brush shaft arrangement for total subgingival periodontal pocket disinfection and tooth surface rinsing. The arrangement of the bristle shaft bundle 1 is pointed towards the bottom which has a coaxial circular gap 2. This bristle shaft bundle 1 is also shown in FIG. 5 as the enlarged detail "B" of FIG. 1. Bundle 1 is formed, aligned and clamped in by the cup ring-shaped blade 3 in the upper seal of the internal cup D and a cup ring-shaped blade 5 formed as cone 4 in the upper portion of the external cup E. The internal cup D and the external cup E together form the rotating gingival rim cup. The bristle shaft bundle 1 forms a conical trapeze-shaped space 6 which serves for accommodating a preparation with alcohol at an effective percentage for the overall preparation.

A reinforced, innermost, rotationally circular bristle shaft 7 with the shaft arrangement 8 seen in FIG. 2 which shows the enlarged detail "A" of FIG. 1 extends up to the external adjoining. An individual, second, reinforced, rotationally circular bristle shaft 9 penetrates with the pointed bristle shaft arrangement 10 of the stepped section 11 into the subgingival periodontal pocket up to the ligamentum circulare. The bristle shaft 9 resists to bending of the bristle shaft 7. The pointed bristle shaft arrangement 10 also brings about a simultaneous disinfection of the periodontal pocket rim together with the biological preparation. The conic trapeze space 6 allows for rinsing of the tooth surfaces. The projecting tips 13, 8, 14, 15 of the bristle shaft 7 reach its wear and tear mark 1 in the course of wear thus determining the time for renewal of the bristle shaft bundle with the bristle shaft arrangements. The internal shape of the external cup E and the external shape of the internal cup D establish a situation wherein the bristle shaft bundle 1 located between them is drawn coaxially into gap 2. The projecting bristle shaft bundle 1 between the cup ring blade 3 and the corrugated bristle shaft arrangements 8 as shown on the internal side of the reinforced bristle shaft 7 has a cylinder directed upwards towards the free bristle shaft corrugation arrangements 8 whereas the external surface of the bristle shaft bundle 1 between the conic ring blade 5 and the bristle shaft corrugated arrangement 8 has two conic trapeze surfaces in such a way that the part projecting out of the gingival rim cup runs cylindrically between the cup ring blade 5. The point 16 and part of the conic section 16 to 20 connected on top with the pointed bristle shaft arrangements and the bristle shaft bundle steps 17, 18, 19, 20 proceed inwards in a conical trapeze shape. The innermost two bristle shafts 7, 9 must project beyond the pointed stepped conic section 16 to 20 as shown in FIG. 2 of the detail "A" of FIG. 1.

FIG. 6 shows four of the possible variations of the ring-blade shape structure of the external periphery of the external cup E. The external contour 5-4 and thus the internal contour 5-21 at the intersection edge of the external cup E can be formed in each ease with the angular orientation in accordance with a specific requirement. Virtually any angle is available within practical limits.

FIG. 7 shows a cylinder screw 22 with thread 23 and head milling 24. Screw 22 is held in a cylindrical axial hole 25 of the centering pin 26 of the external cup E. Hole 25 accommodates the cylinder screw 22 with a tight fit. By this means the lower edge 27 of the head of the flanged rivet portion 28 of the centering pin 26 is tensioned against the rotary surface 32 of the shaft carrier 29.

FIG. 8 shows the shaft carrier 29 which accommodates the thread part 23 of the cylinder screw 22 in an axial threaded pocket hole 30 until the flat contact surface 31 of the external cup E contacts the upper flat surface 32 of the shaft carrier 29. The shaft carrier 25 has at point 33 a cross-hole and a thread 34. The shaft end 35 is pointed.

FIG. 9 illustrates the essential elements of the drive casing 36 in which the shaft carrier 29 is inserted. More precisely shaft carrier 29 is inserted in the bearing bush 37 with the cross-hole 37a on one side. Shaft carrier 29 can be screwed in and out with its thread part 23 in the coupling thread 38. The drive unit is switched on by press button 40 by means of battery cells located in the surrounding periodontal pocket unit. The rear part of FIG. 9 is characterised by a screwed-on sealing cap 39, thus permitting the batteries to be changed.

It will be understood that each of the elements described above, or two or more together, may also find a useful application in other types of bristle shafts differing from the types described above.

While the invention has been illustrated and described as embodied in a bristle shaft, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A bristle shaft device for use in disinfecting subgingival parodontal pockets, parodontal pocket edges and tooth surfaces, the device comprising:
    a rotationally symmetrical gingival edge cup having an axis and an external periphery; and
    means for disinfecting subgingival parodontal pockets, parodontal pocket edges and dental surfaces and including a plurality of coaxial bristle shafts arranged coaxially in a ring and held in position by said cup, said shafts projecting from said external periphery, said plurality of bristle shafts being formed as individual radially adjacent bristle layers, one of said layers extending beyond other layers so as to have an exposed end for penetrating into a subgingival parodontal pocket up to a ligamentum circulare, another of said layers being arranged adjacent to said one layer for resisting a bending of said exposed end, the remaining layers of said bristle layers being formed as multiple stepped layers which drop off in steps from each other in a radially outward direction for further reinforcing said one layer and said another layer, said one layer being radially innermost of the rest of the layers, said one layer and said another layer projecting beyond said remaining layers, said exposed end of said one layer being formed with a projection so as to form an individual, coaxial bristle shaft ring.

2. The device as defined in claim 1, wherein said projection at said end of said one innermost layer has a corrugated shape.

3. The device as defined in claim 1, wherein said projection at said end of said one innermost layer has a serrated shape.

4. The device as defined in claim 1, wherein said projection at said end of said one innermost layer has a roof-like shape.

5. The device as defined in claim 1, wherein said projection at said end of said one innermost layer has a pointed inclined-like shape.

6. The device as defined in claim 1, wherein said plurality of said shafts form a cylinder which encloses a central substantially cylindrical space for receiving a biological preparation for disinfection, said disinfecting means further including means for simultaneously bringing about a disinfection of a parodontal pocket edge when a biological preparation is received in said space and including said another bristle shaft having pointed inclined bristles which taper radially outward from said innermost layer.

7. The device as defined in claim 1, wherein said plurality of bristle shafts are arranged so as to form a circular cylinder, said plurality of bristle shafts constituting a bristle shaft bundle and defining an inner cylindrical space which receives a biological preparation for disinfection.

8. The device as defined in claim 1, wherein said external periphery of said cup has an outermost edge portion forming a sharp sealing edge, said edge portion being arranged in contact with said plurality of bristle shafts to define an angle of emergence of said plurality of bristle shafts from said external periphery.

9. The device as defined in claim 8, wherein said edge portion contacts said bristle shafts so that said bristle shafts emerge from said external periphery of said cup directed inwardly.

10. The device as defined in claim 8, wherein said edge portion contacts said bristle shafts so that said bristle shafts emerge from said external periphery of said cup directed outwardly.

11. The device as defined in claim 8, wherein said edge portion contacts said bristle shafts so that said bristle shafts emerge from said external periphery of said cup directed vertically.

12. The device as defined in claim 1, further comprising:
    means for connecting said cup to a bushing of a drive means for a drive engagement therewith and including a shaft carrier having a threaded portion with a pointed end, said threaded portion and said pointed end being formed so as to be insertable into the bushing, said shaft carrier also having a transverse hole passing therethrough.

13. The device as defined in claim 1, further comprising:
    means for rotatably driving said cup and therefore said bristle shafts.

14. The device as defined in claim 13, wherein said driving means include a driving element, a casing housing having an external periphery, and a pushbutton arranged in said casing so as to not project beyond said external periphery of said casing, said pushbutton being operatively connectable to said driving element for switching on said driving element.

15. The device as defined in claim 14, further comprising means for connecting said cup to said driving means.

16. The device as defined in claim 15, wherein said connecting means includes a screw with a shaft and also includes an axial passage formed axially through said cup, said axial passage being formed to receive said screw so that when said screw is inserted into said axial passage, at least a portion of said shaft passes through said axial passage.

17. The device as defined in claim 1, wherein said another layer is formed so as to have a predetermined wear and tear location such that when said one layer wears away to reach said predetermined wear and tear location of said another layer, said one layer is ready for replacement.

* * * * *